(12) United States Patent
Filho et al.

(10) Patent No.: US 6,753,458 B1
(45) Date of Patent: Jun. 22, 2004

(54) PROCESS FOR OBTAINING TRANSGENIC LEGUMINOUS PLANTS (LEGUMINOSAE) CONTAINING EXOGENOUS DNA

(75) Inventors: Elibio Leopoldo Rech Filho, Brasília (BR); Francisco José Lima Aragão, Brasília (BR)

(73) Assignee: EMBRAPA-Empress Brasileira de Pesquisa Agropecuária, Brasília (BR)

( * ) Notice: Subject to any disclaimer, the term of this patent is extended or adjusted under 35 U.S.C. 154(b) by 0 days.

(21) Appl. No.: 09/509,982

(22) PCT Filed: Oct. 7, 1997

(86) PCT No.: PCT/BR97/00053

§ 371 (c)(1),
(2), (4) Date: Jul. 6, 2000

(87) PCT Pub. No.: WO99/18223

PCT Pub. Date: Apr. 15, 1999

(51) Int. Cl.$^7$ ............................ C12N 15/82; A01H 4/00
(52) U.S. Cl. ........................ 800/278; 435/430; 435/470; 800/300; 800/312; 800/313
(58) Field of Search ................................ 435/468, 469, 435/470, 426, 430, 430.1; 800/278, 293, 300, 418, 419, 312

(56) References Cited

U.S. PATENT DOCUMENTS

| | | | | |
|---|---|---|---|---|
| 4,940,835 A | * | 7/1990 | Shah et al. ............... | 435/320.1 |
| 5,477,000 A | | 12/1995 | Saxena et al. ............... | 435/430 |
| 5,565,346 A | | 10/1996 | Facciotti ..................... | 800/293 |
| 5,589,583 A | | 12/1996 | Klee et al. .................. | 800/298 |
| 5,830,728 A | * | 11/1998 | Christou et al. .......... | 435/320.1 |

FOREIGN PATENT DOCUMENTS

| | | |
|---|---|---|
| EP | 0301749 | 2/1989 |
| EP | 0430511 | 6/1991 |
| EP | 0 430 511 A1 * | 6/1991 |
| EP | 0519758 | 12/1992 |
| FR | 2736929 | 1/1997 |
| WO | WO92/04449 | 3/1992 |

OTHER PUBLICATIONS

McCabe et al, Stable Transformation of Soybean By Particle Acceleration, Aug. 1988, Biotechnology, vol. 6, pp. 923–926.*

Aragao, F, J. L. et al. "Morphologial Factors Influencing Recovery of Transgenic Bean Plants (*Phaseolus Vulgaris L.*) of a Carioca Cultivar" International Journal of Plant Sciences 158 (2) 1997, p. 157–163.

Christou P. "Strategies For Variety–Independent Genetic Transformation Of Important Cereals, Legumes and Woody Species Utilizing Particle Bombardment" vol. 85 1995, p. 13–27.

McCabe, D, et al. "Stable Transformation of Soybean (Glycine Max) By Particle Acceleration" *Biotechnology* vol. 6, No. 8, Aug. 1988, p. 923–926.

Christou, P., et al. "Soybean Genetic Engineering–Commercial Production of Transgenic Plants" *Trends In Biotechnology* vol. 8, No. 6, Jun. 1990, p. 145–151.

Russell, D.R., et al. Stable Transformation Of Phaseolus Vulgaris Via Electric–Discharge Mediated Particle Acceleration *Plant Cell Reports* vol. 12, 1993, p. 165–169.

Brar, G., et al. "Recovery of Transgenic Peanut (*Arachnis hypogaea L.*) Plants Form Elite Cultivars Utilizing ACCELL Technology" *The Plant Journal* vol. 5, No. 5, 1994, p. 745–753.

Kononowicz, A., et al. "Genetic Transformation Of Cowpea Vigna–Unguiculata Using Microprojectile Bombardment and Agrobacterium–Tumefaciens Infection" *Plant Physiol* (ROCKV) 102 (1 SUPL), May 1993, p. 165. (Abstract).

Zhou H. et al. "Glyphosate–Tolerant CP4 and GOX Genes As A Selectable Marker In Wheat Transformation" *Plant Cell Reports* vol. 15, No. 3/04, Dec. 1, 1995, p. 159–163.

* cited by examiner

*Primary Examiner*—Amy J. Nelson
*Assistant Examiner*—David H Kruse
(74) *Attorney, Agent, or Firm*—Smith, Gambrell & Russell

(57) ABSTRACT

The invention relates to a process of selecting germ line-transformed leguminous plants by introducing a DNA construct encoding a protein to confer imidazolinone or glyphosate resistance and selecting transformed shoots with a low concentration of herbicide.

9 Claims, 2 Drawing Sheets

Figure 1A
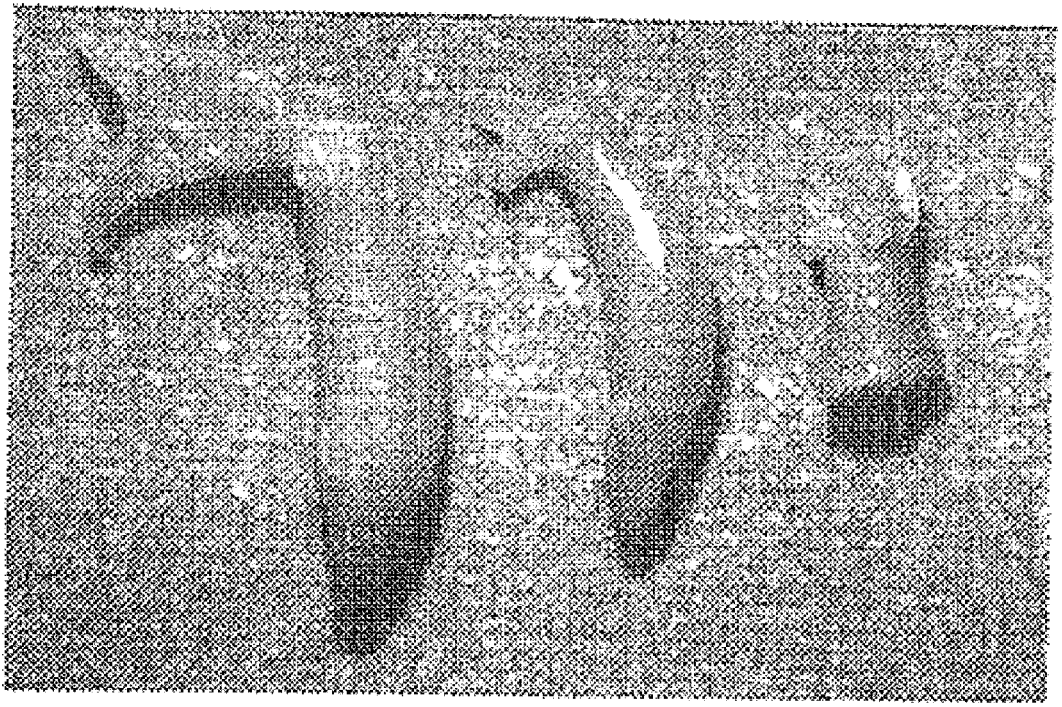
Figure 1B

PROCESS FOR OBTAINING TRANSGENIC LEGUMINOUS PLANTS (LEGUMINOSAE) CONTAINING EXOGENOUS DNA

This is the National Stage of International Appln. No. PCT/BR97/00053, filed Oct. 7, 1997 in English.

FIELD OF THE INVENTION

The present invention refers to the use of biobalistic for introducing exogenous genes into a vegetable tissue and obtaining transgenic leguminous plants by regenerating the transformed tissue.

BACKGROUND OF THE INVENTION

The use of genetic engineering techniques for introducing genes which are responsible for agronomic characteristics of interest may facilitate the development of new varieties of LEGUMINOSAE. The obtaintion of a transgenic plant requires methods of introducing the exogenous DNA into the vegetable tissue and regenerating the whole plant from such genetically transformed tissue. Depending upon the species to be transformed, various types of tissue have been used for the introduction of an exogenous DNA, the meristematic tissue been preferably employed in various transformation processes, primarily due to the ease regeneration of a plant from this type of tissue. Various processes have been proposed for introducing exogenous genes into apical meristematic cells of LEGUMINOSAE, among which the following can be pointed out: a) the Agrobacterium system; b) a system related to tissue electroporation and c) the biobalistic system. The introduction and integration of exogenous DNA into cells of LEGUMINOSAE have been demonstrated by various scientists and described in different publications such as (Aragão F. J. L., Grossi-de-Sá M. F., Almeida E. R, Gander E. S. Rech E. L. (1992); Particle bombardment mediated expression of a Brazil nut methionine-rich albumin in bean (*Phaseolus vulgaris* L.); Plant Molecular Biology 20:357–359. Lewis, M. F. & Bliss, F. A. (1994); Tumor formation and beta-glucuronidase expression in *Phaseolus vulgaris* L inoculated with *Agrobacterium tumefactiens*. Journal of the American Society for Horticultural Science; 119:361–366, Dillen W. Engler G. Van Montagu M. & Angenon G. (1995); Electroporation-mediated DNA delivery to seedling tissues of *Phaseolus vulgaris* L (common bean), Plant cell Reports, 15:119–124.

However, the low obtaintion frequency of the genetically transformed tissue, the low capacity of regenerating a fertile plant from said transformed tissue, together with the use of transformation methods the efficiency of which depends upon the genotype, have rendered it difficult to obtain transgenic leguminous plants (Brasileiro A. C. M.; Aragão F. J. L.; Rossi S. Dussi D. M. A.; Barros L. M. G.; & Rech E. L. (1996)—Susceptibility of common and tepary beans to Agrobacterium ssp. strains and improvement of Agrobacterium-mediated transformation using microprojectile bombardment J. Amer. Soc. Hort. Sci. 12:810–915 and Dillen W.; Van Montagu M. & Angenon G. (1995) Electroporation-mediated DNA delivery to seedling tissues of *Phaseolus vulgaris* L. (common bean). Plant Cell Reports 15:119–124).

With the development of the biobalistic process for the direct introduction of genes into vegetable cells at the end of the '80 (Sanford J. C. Klein T. M., Wolf E. D. & Allen N. (1987) Delivery of substances into cell tissues using a particle bombardment process; Journal of Particle Science and Technology, 5:27–37), a great number of transgenic plants of several species have been obtained, including those species which proved to be recalcitrant to the transformation by the using other methods. This is due to the fact that it has become possible to introduce and express exogenous genes in any kind of vegetable tissue. Thus, any type of tissue having a potential ability to regenerate a whole fertile plant is suitable for transformation.

The biobalistic process was proposed by Sanford with a view to introduce genetic material into the nuclear genome of higher plants. Since then its universality of application has been appraised, and it has proved to be an effective and simple process for the introduction and expression of genes into bacteria, protozoa, fungi, algae, insects, vegetable and animal tissue, as well as isolated organcils as chloroplast and mitochondria, according to the results observed by Sanford J C, Smith F D & Russel J. A. (1993) Optimizing the biobalistic process for different biological application. Methods in Enzymology: 217:413–510. In the specialized literature there are several other examples of the use of biobalistic for the obtaintion of transgenic organisms such as, for instance, U.S. Pat. Nos. 5,565,346, 5,489,520 and WO 96/04392, among others.

In biobalistic microprojectiles accelerated at high speed are used for carrying and introducing nucleic acids and other substances into cells and tissues in vivo (Rech E. L. & Aragão F. J. L. (1997). The ballistics process—In: Brasileiro A. C. M. & Carneiro. V. T. C. (Ed)—Manual of genetic transformation of plants: EMBRAPA/Cenargen. This process has also been called as method of bombardment with microprojectiles, "gene gun" method, particle-acceleration method, among others. Different systems have been developed and constructed which are capable of accelerating microparticles (made of tungsten or gold), coated with nucleic acids sequences, at speeds higher than ink 1500 km/h-1. All these systems are based on the generation of a shock wave with enough energy for displacing a carrying membrane containing the microparticles coated with DNA. The shock wave can be generated by a chemical explosion (dry gunpowder), a discharge of helium gas under high pressure, by vaporization of a drop of water through a electric discharge at high voltage and low capacitance or at low voltage and high capacitance.

Those systems which use helium gas under high pressure and electric discharge have shown a wide spectrum of utilization. The accelerated particles penetrate the cellular wall and membrane in a non-lethal way, locating themselves randomly in the cellular organells. Then the DNA is dissociated from the microparticles by the action of the cellular liquid, and the process of integrating the exogenous DNA in the genome of the organism to be modified takes place (Yamashita T. lada, A. & Morikawa H. (1991)—Evidence that more than 90% of β-glucuronidase-expressing cells after particle bombardment directly receive the foreign gene in their nucleus; Plant Physiol. 97:829–831).

In spite of the efficiency and universality of utilization of the biobalistic process, it depends upon the optimization of various physical and biological parameters, which is fundamental to the effective introduction of heterologous genes into a vegetable tissue.

For the obtaintion of transgenic plants from the apical region of embrionic axis, there are two essential requirements, namely: 1) introduction of exogenous genes with high frequencies into the cells of the apical regions, and 2) integration of erogenous genes into the vegetable genome, and 2) regeneration and production of fertile transgenic plants from the resulting transformed cells.

With the development of the biobalistic process the in situ direct transformation of cells of the apical meristem is now possible. However, the development and further production of fertile transgenic plants require the regeneration and production of the plant from the transformed cells.

During the last few decades several attempts have been made to obtain the regeneration of fertile plants of commercially important LEGUMINOSAE. Although many advances have been achieved, no effectively positive results have been obtained yet. For instance, some methodologies of multiple shooting of apical and lateral meristems of embryos in different LEGUMINOSAE have been developed. However, these systems still present serious disadvantages.

Other regeneration systems developed for certain LEGUMINOSAE such as peanuts and soybeans involve the induction of somatic embryogenesis from mature and immature embryos cultivated at high doses of 2,4-D. However, the practical use of this system is limited since it is restricted to determined varieties, in addition to the fact that induction of unwanted genetic variations (somaclonal variation) also occurs with the consequent production of transgenic plants with their inherent agronomic characteristics changed.

Thus, the systems already known for the obtaintion of transgenic plants of LEGUMINOSAE based on the transformation of meristematic cells of the apical region, by using the biobalistic process present the disadvantages of impossibility of selecting the transformed cells, low production frequencies of transgenic plants and high frequency of chimeras (plants with an organ or groups of some transgenic cells and other non-transgenic cells).

It is therefore, the objective of the present invention to provide a process with high production frequency for the obtaintion of transgenic leguminous plants containing an exogenous DNA and which enables the selection of the transformed cells, the latter maintaining the agronomic characteristics of the plants from which they have originated.

SUMMARY OF THE INVENTION

The present invention refers to a process for producing transgenic leguminous plants containing exogenous DNA, which comprises the steps of:

a) introducing exogenous genes into cells of the apical meristem of the embryonic axis of leguminous plants by the biobalistic method:

b) inducing the multiple shooting of the cells in the apical meristematic region modified in step (a) by cultivating said embryonic axis in a medium containing a multiple shooting inducer; and c) selecting the meristematic cells of the apical region as obtained in step (b) by further cultivation of said embryonic axis in a medium containing a molecule which concentrates in the apical meristematic region of said leguminous embryos.

BRIEF DESCRIPTION OF THE FIGURES

FIG. 1A shows the meristematic apical region of embryonic axis black beans;

FIG. 1B shows the process of explant bombardment of black beans with the removal of the leaves.

DETAILED DESCRIPTION OF THE INVENTION

Figure 2:
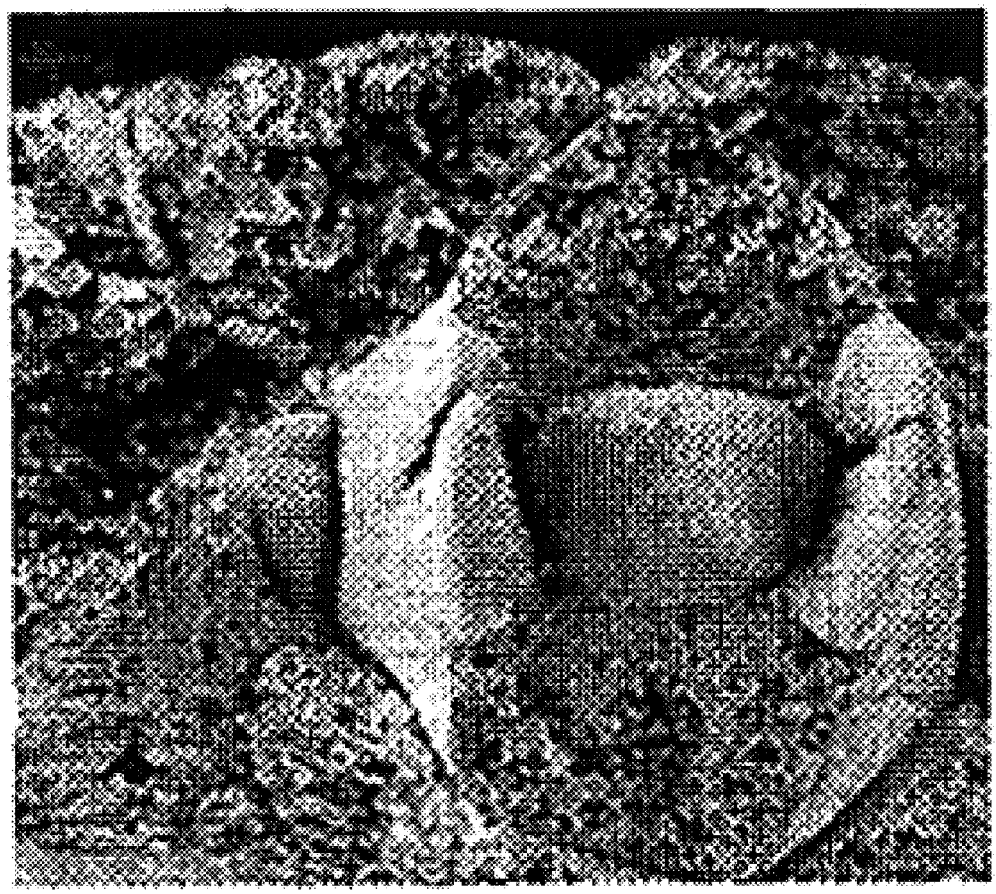
FIG. 2 shows the meristematic apical region of embryonic axis of soybean.

It has now been surprisingly found that a biobalistic process for transforming leguminous plants by introducing an exogenous DNA into their apical meristematic region, associated with further steps of multiple shooting and subsequent selection of the transformed plants, by using, for this purpose, specifically the embryonic axis of said cells, enables the regeneration and production of transgenic plants with a production frequency of the order of 10%. This value represents a magnitude of about 200 times as high as the frequencies obtained by the processes known at present, which are of the order of 0.03%–0.05%. In addition the process of the present invention enables the obtaintion of transgenic plants in a period of time shorter than those described in the prior art.

The process as claimed now is suitable for transformation, regeneration and selection of any leguminous plant such as soybeans, beans, cowpea and peanuts.

According to the present invention, the embryonic axis of the apical meristematic cells of leguminous plants to be transformed are prepared in laboratories in a conventional way for the bombardment (biobalistic) process. Of course, the genes to be used for the bombardment will depend upon the specific objective of each process in question, that is to say, they will be chosen in accordance with the new characteristic which one desires to impart to the transformed plant. For instance, in the case where the objective of the process is to obtain plants resistant to herbicides, genes which impart such a resistance to herbicides would be utilized.

After the bombardment, the embryonic axis are then contacted with a culture medium containing a multiple shoot inducer and should be maintained in this medium for a period of time sufficient to guarantee the desired induction, preferably during a period ranging from 16 to 120 hours. In a preferred embodiment of the invention, cytokinins, namely 6-benzylaminopurin (BAP) or tidiazuron (TDZ), are used as a multiple shooting-inducing agent. An additional advantage of the present invention is that the now claimed process enables the multiple shooting to be completed in a relatively short period of time, thus avoiding the occurrence of genetic variations that are common to other known processes.

After the period of multiple shooting induction, the embryonic axis should be transferred to an additional culture medium containing the agent which will promote the selection of the transformed cells. As in the bombardment process, the selection agent will, be chosen according to the final objectives of the process. In the case of transgenic plants which are transformed with genes which impart resistance to herbicides, the selection agent will be the herbicide to which the plant should have developed resistance. Examples of herbicides which are particularly usable in the process of the invention is the herbicide Glyphosate (sold by Monsanto Company and called "Round Up") and the herbicides selected from the family of the imidazolinones such as Imazapyr (sold by American Cyanamid Company). During the step for selecting the transformed cells, a molecule which concentrates in the apical meristematic region of leguminous embryos, such as the above-cited herbicides, for instance, is carried through the vascular system of the embryoonic axis, then concentrating in the apical meristematic region. In this way, it is possible to carry out the selection of the cells without deleterious effects to the embryonic axis.

The invention can be better understood with the help of the examples given below, which are merely illustrative and the parameters and conditions described should not be regarded as being limiting of the invention.

EXAMPLES

Preparation of the Embryonic Axis for Bombardment (Biobalistic)

Ripe seeds of LEGUMINOSAE selected from the group comprising soybeans, beans and peanuts were disinfected in 70%-ethanol for 1 minute and in 1.0%-sodium hypochlorite for 20–30 minutes. The disinfected seeds were washed with sterile distilled water and incubated for 16–18 hours in sterile distilled water at room temperature.

The seeds were then opened for removal of the embryonic axis. The primary leaves were cut so as to expose the region of the apical meristem. In the case of beans, the radicle portion was also cut whereas for the other LEGUMINOSAE there was no need for cutting the radicle portion.

LEGUMINOSAE meristematic apical regions of embrionic axis of black beans and of soybean are illustrated in FIGS. 1 and 2, respectively. FIG. 1A specifically shows the meristematic apical region of the meristematic apical region whereas FIG. 1B demonstrates the process of explant for bombardment with the removal of the primary leaves in order to expose the apical meristem and allow the removal of the radicle.

The axis of the embryos were disinfected in 0.1%-sodium hypochlorite for 10 minutes and washed 3 times in sterile distilled water. Then the embryonic axis were placed in the culture plates containing the bombardment medium (10–15 axis/plate), said bombardment medium (herein after called BM) consisting of a medium of Murashig and Skoog (1962), here referred to as MS, supplemented with 3% of sucrose, 0.7% phytagel, pH 5.7. The axis were arranged in a circle, equidistant by 6–12 mm from the center of the plate and with a region of the apical meristem directed upwards.

After positioning the embryo axis, it was observed under a stereomicroscope that the meristematic region was covered with a liquid film and, therefore, the cover of the plate was opened under laminar flow for 1–2 minutes right before the bombardment, in order to prevent the liquid film on the meristematic surface from reducing the penetration of the microparticles and, consequently, reducing the level of expression of the introduced gene.

Once the material to be transformed had been positioned on the plate containing the bombardment medium BM, it was bombarded with the gene of interest. In this case, various vectors containing genes which create resistance to the herbicides Glyphosate and Imazapyr were used.

Preparation of the Micropanicles

The microparticles responsible for carrying the exogenous DNA into the cells were sterilized and washed. 60 mg of microparticles of tungsten M10 (Sylvania).or gold (Aldrich, 32,658-5) were weighed, transferred to a microcentrifuge tube, to which 1.0 ml of 70% ethanol was added. The mixture was vigorously stirred and kept under stirring for 15 minutes at the lowest speed of the stirrer. 15.000 g was centrifuged for 5 minutes and the supernatant was removed and discarded with the help of a micropipette of 1,000 µl, 1 ml of sterile distilled water was added and mixed vigorously in a stirrer and centrifuged as in the preceding step. The supernatant was discarded; and the washing operation was repeated two more times.

After the last washing, the supernatant was discarded, and the microparticles were again suspended in 1 ml of 50% glycerol (v/v). Equal parts of glycerol and distilled water were mixed, the mixture was autoclaved and kept at room temperature.

Then the exogenous DNA was precipitated onto the microparticles and, for this purpose, an aliquot part of 50 µl of the microparticle suspension (60 mg/ml) was transferred to a microcentrifuge tube. From 5 to 8 ml of DNA (1 mg/µl) was added. The mixture was rapidly homogenized (3–5 seconds) by stirring the outer part of the tube with help of the fingers. 50 µl of $CaCl_2$ 2.5 M was added, rapidly homogenized and 20 µ of spermidine 0.1 M (Sigma S-0266) was added, which is an extremely hygroscopic and oxidizable reactant.

The resulting mixture was incubated at room temperature under slow stirring for 10 minutes. centrifuged for 10 sec, and the supernatant was carefully removed. 150 µl of absolute ethanol was added, and then the outer part of the tube was again stirred with the help of the fingers. The resulting mixture was centrifuged at 15,000 g for 10 seconds, and the supernatant was removed. The preceding step was repeated, adding 24 µl of absolute ethanol, vigorously homogenized and sonicated for 1–2 seconds.

Then samples of 3.2 µl of the solution was distributed in the central region of each carrying membrane previously positioned on a membrane support. Each precipitation was sufficient for preparing 6 carrying membranes containing microparticles covered with the DNA of interest. The discs containing the microparticles covered with DNA were immediately stocked on a plate containing drying material (silica gel) and placed in a desiccator.

The bombardment of the apical meristematic region of the embryonic axis of the leguminous plants was carried out with a microparticle accelerator which utilizes high pressure of helium gas, as described in Aragão et al—1996.

Example 1

Obtaintion of Transgenic Plants of Soybean (*Glycine max*, (L.) Merril), Through the Selection With the Herbicide Imazapyr Immediately after the bombardment of the embryonic axis with the microparticles covered with an exogenous DNA which imparts resistance to Imazapyr, the embryonic axis were transferred from the bombardment medium (BM) to culture plates containing multiple shooting-inducing medium (IM) (MS medium supplemented with 22.2 µl BAP, 3% sucrose, 0.6% of agar, pH 5.7). The bombarded embryonic axis remained immersed in the IM for 16–24 hours in darkness conditions, at 27° C. in order to induce multiple shooting. After this period had passed, the embryonic axis were transferred to plates with culture medium containing herbicide (CMH) (SM medium, 3% sucrose, 500–1000 nM of Imazapyr, 0.7% of agar, pH 5.7) and kept in a growth chamber at a temperature of 27° C. with 16 hours photoperiod (50 umols $m^{-2}s^{-1}$) until the induction of multiple shooting.

The shoots that reached 2–4 cm length were transferred to a culture medium MS1S (MS, 1% of sucrose, 0.8% of agar, pH 5.7), with photoperiod of 16 hours (50 µmols $m^{-2}s^{-1}$) at 27° C. to enable the plantlets to grow and take root A section of 1 mm was removed from the base of the stem and leaf for analysis of the expression of the exogenous gene. The shoots expressing the exogenous DNA were individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 2

Obtaintion of Transgenic Plants of Soybean (*Glycine max*, (L.) Merril), With the Herbicide Glyphosate Immediately after the bombardment of the axis of the embryonic axis with the microparticles covered with an exogenous DNA which imparts resistance to Glyphosate, the embryonic axis were transferred from the bombardment medium (BM) to culture plates containing multiple shooting inducing medium (IM) (MS medium supplemented with 22.2 μl BAP, 3% sucrose, 0.6% of agar, pH 5.7). The bombarded embryonic axis remained immersed in the IM for 16–24 hours in darkness conditions, at 27° C. in order to induce multiple shooting. After this period had passed, the embryonic axis were transferred to plates with culture medium containing herbicide (CMH) (SM medium, 3% sacrose, 300–1000 nM of Glyphosate, 0.7% of agar, pH 5.7) and kept in a growth chamber at a temperature of 27° C. with 16 hours photoperiod (50 μmols m–2s–1) until the induction of multiple shoots.

The shoots that reached 2–4 cm length were transferred to a culture medium MS1S (MS. 1% of sucrose, 0.8% of agar, pH 5.7), with photoperiod of 16 hours (50 μmols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 3

Obtaintion of Transgenic Plants of Beans (*Phaseolus vulgaris* L.), Through Selection With the Herbicide Imazapyr Immediately after the bombardment of the axis of the embryonic axis with the microparticles covered with an exogenous DNA which imparts resistance to lmazapyr, the embryonic axis were cultivated in the same culture medium (BM) for 7 days at a temperature of 27° C. with 16 hours photoperiod (50 μmols $m^{-2}s^{-1}$) for induction of the multiple shoots. After this period, the embryonic axis which germinated were transferred to a "Magenta"-type box containing the culture medium MSBH (MS medium supplemented with 44.2 μM BAP, 3% of sucrose, 100–500 nM of Imazapyr, 0.8% of agar, pH 5.7), for 7 days at a temperature of 27° C. with 16 hours photoperiod (50 μmols $m^{-2}s^{-1}$) to reduce the total number of multiple shoots. Then the embryonic axis were again transferred to the "Magenta"-type culture box containing the culture medium MS3S (SM supplemented with 44.2 μM BAP, 3% of sucrose, 0.8% of agar, pH 5.7) at a temperature of 27° C. with 16 hours photoperiod (50 μmols $m^{-2}s^{-1}$) to enable the elongation of the multiple shoots. After two weeks the axis of embryos began to emit shoots.

The shoots that reached 2–4 cm length were transferred to a culture medium MS1S (MS, 1% of sucrose, 0.8% of agar, pH 5.7). with photoperiod of 16 hours (50 μmols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed The plantlets were transferred to vessels containing soil for the production of seeds.

Example 4

Obtaintion of Transgenic Plants of Beans (*Phaseolus vulgaris* L.), Through Selection With the Herbicide Glyphosate Immediately after the bombardment of the embryonic axis with the microparticles covered with an exogenous DNA which imparts resistance to Glyphosate, the embryonic axis were cultivated in the same culture medium (BM) for 7 days at a temperature of 27° C. with 16 hours photoperiod (50 μmols $m^{-2}s^{-1}$) for induction of the multiple shoots. After this period, the embryonic axis which germinated were transferred to a "Magenta"-type box containing the culture e medium MSBH (MS medium supplemented with 44.2 μM BAP, 3% of sucrose, 200–1000 nM of Glyphosate, 0.8% of agar, pH 5.7), for 7 days at a temperature of 27° C. with 16 hours photopeiod (50 μmols $m^{-2}s^{-1}$) to reduce the total number of multiple shoots. Then the embryonic axis were again transferred to the "Magenta"-type culture box containing the culture medium MS3S (SM supplemented with 44.2 uM BAP, 3% of sucrose, 0.8% of agar, pH 5.7) at a temperature of 27° C. with 16 hours photoperiod (50 μmols $m^{-2}s^{-1}$) to enable the elongation of the multiple shoots. After two weeks the axis of embryos began to emit shoots.

The shoots that reached 2–4 cm length were transferred to a culture medium MS1S (MS, 1% of sucrose, 0.8% of agar, pH 5.7), with photoperiod of 16 hours (50 μmols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 5

Obtaintion of Transgenic Plants of Cowpea (*Vignia unguiculata*), Through Selection With the Herbicide Imazapyr Immediately after the bombardment of the embryonic axis with the microparticles covered with an exogenous DNA which imparts resistance to Imazapyr, the embryonic axis were cultivated in the same culture medium (MB) for 7 days at a temperature of 27° C. with 16 hours photoperiod (50 μmols $m^{-2}s^{-1}$) for induction of the multiple shoots. After this period, the embryonic axis which germinated were transferred to a "Magenta"-type box containing the culture medium MSBH (MS medium supplemented with 5–50 μM BAP, 3% of sucrose, 100–500 nM of IMAZAPYR, 0.8% of agar, pH 5.7), for 7 days at a temperature of 27° C. with 16 hours photoperiod (50 umols $m^{-2}s^{-1}$) to reduce the total number of multiple shoots. Then the embryonic axis were again transferred to the "Magenta"-type culture box containing the culture medium MS3S (MS supplemented with 20–50 μM BAP, 3% of sucrose, 0.8% of agar, pH 5.7) at a temperature of 27° C. with 16 hours photoperiod (50 μmols $m^{-2}s^{-1}$) to enable the elongation of the multiple shoots. After two weeks the axis of embryos began to emit shoots.

The shoots that reached 2–4 cm length were transferred to a culture medium MS1S (MS, 1% of sucrose, 0.8% of agar, pH 5.7), with photoperiod of 16 hours (50 $\mu$mols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask, Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 6

Obtaintion of Transgenic Plants of Cowpea (*Vignia unguiculata*), Through Selection With the Herbicide Glyphosate Immediately after the bombardment of the axis of the embryonic axis with the microparticles covered with an exogenous DNA which imparts resistance to Glyphosate, the embryonic axis were cultivated in the same culture medium (BM) for 7 days at a temperature of 27° C. with 16 hours photoperiod (50 $\mu$mols $m^{-2}s^{-1}$) for induction of the multiple shoots. After this period, the embryonic axis which germinated were transferred to a "Magenta"-type box containing the culture medium MSBH (MS medium supplemented with 5–50 $\mu$M BAP, 3% of sucrose, 200–1000 nM of Glyphosate, 0.8% of agar, pH 5.7), for 7 days at a temperature of 27° C. with 16 hours photoperiod (50 umols m–2s–1) to reduce the total number of multiple shoots. Then the embryonic axis were again transferred to the "Magenta"-type culture box containing the culture medium MS3S (MS supplemented with 20–50 $\mu$M BAP, 3% of sucrose, 0.8% of agar, pH 5.7) at a temperature of 27° C. with 16 hours photoperiod (50 $\mu$mols $m^{-2}s^{-1}$) to enable the elongation of the multiple shoots. After two weeks the axis of embryos began to emit shoots.

The shoots that reached 2–4 cm length were transferred to a culture medium MS1S (MS, 1% of sucrose, 0.8% of agar, pH 5.7), with photoperiod of 16 hours (50 $\mu$mols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 7

Obtaintion of Transgenic Plants of Peanuts (*Arachis hypogea*L.), Through Selection With the Herbicide Imazapyr Immediately after the bombardment of the axis of embryonic axis with the microparticles covered with an exogenous DNA which imparts resistance to Imazapyr, the embryonic axis were cultivated in the same culture medium (BM) for 7 days at a temperature of 27° C. with 16 hours photoperiod (50 $\mu$mols $m^{-2}s^{-1}$) for induction of the multiple shoots. After this period, the embryonic axis which germinated were transferred to a "Magenta"-type box containing the culture medium MSBH (MS medium supplemented with 5–50 $\mu$M BAP, 3% of sucrose, 100–500 nM of IMAZAPYR, 0.80% of agar, pH 5.7), for 7 days at a temperature of 27° C. with 16 hours photopeoiod (50 $\mu$mols $m^{-2}s^{-1}$) to reduce the total number of multiple shoots. Then the embryonic axis were again transferred to the "Magenta"-type culture box containing the culture medium MS3S (MS supplemented with 44.3 $\mu$M BAP, 3% of sucrose, 0.8% of agar, pH 5.7) at a temperature of 27° C. with 16 hours photoperiod (50 $\mu$mols $m^{-2}s^{-1}$) to enable the elongation of the multiple shoots. After two weeks the axis of embryos began to emit shoots.

The shoots that reached 2–4 cm length were transferred to a culture medium MS1S (MS, 1% of sucrose, 0.8% of agar, pH 5.7), with photoperiod of 16 hours (50 $\mu$mols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

Example 8

Obtaintion of Transgenic Plants of Peanuts (*Arachis hypogea* L.). Trough Selection With the Herbicide Based on Glyphosate Immediately after the bombardment of the axis of embryonic axis with the microparticles covered with an exogenous DNA which imparts resistance to Glyphosate, the embryonic axis were cultivated in the same culture medium (BM) for 7 days at a temperature of 27° C. with 16 hours photoperiod (50 umols m–2s–1) for induction of the multiple shoots. After this period, the embryonic axis which germinated were transferred to a "Magenta"-type box containing the culture medium MSBH (MS medium supplemented with 5–50 uM BAP, 3% of sucrose, 200–1000 nM of Glyphosate, 0.8% of agar, pH 5.7), for 7 days at a temperature of 27° C. with 16 hours photoperiod (50 umols m–2s–1) to reduce the total number of multiple shoots. Then the embryonic axis were again transferred to the "Magenta"-type culture box containing the culture medium MS3S (MS supplemented with 44.3 $\mu$M BAP, 3% of sucrose, 0.8% of agar, pH 5.7) at a temperature of 27° C. with 16 hours photoperiod (50 $\mu$mols $m^{-1}s^{-1}$) to enable the elongation of the multiple shoots. After two weeks the axis of embryos began to emit shoots.

The shoots that reached 2–4 cm length were transferred to a culture midium MS1S (MS, 1% of sucrose, 0.8% of agar, pH 5.7), with photoperiod of 16 hours (50 $\mu$mols $m^{-2}s^{-1}$) at 27° C. to enable the plantlets to grow and take root. A section of 1 mm was removed from the base of the stem and leaf for analysis of the expression of the exogenous gene. The shoots expressing the exogenous DNA were then individually registered and transferred to a new culture flask. Once the plantlets had taken root, they were transferred to vessels containing an autoclaved soil: vermiculite (1:1) mixture.

The plantlets were covered with a plastic bag closed with an elastic band for 7 days. The elastic band was removed and after 6–7 days the plastic bag was also removed. The plantlets were transferred to vessels containing soil for the production of seeds.

What is claimed is:

1. A process for selecting herbicide resistant germ line-transformed leguminous plants comprising:
   (a) introducing a DNA construct into apical meristem cells of embryonic axes of a leguminous plant by bombardment wherein said DNA constrict comprises a sequence which encodes a protein capable of conferring tolerance to an herbicide selected from the group consisting of an imidazolinone and a glyphosate;
   (b) inducing multiple shoot formation from the transformed apical meristem cells produced in step (a) by culturing said embryonic axes in a culture medium containing a cytokinin; and
   (c) selecting transformed shoots resulting from step (b) by culturing said embryonic axes on a culture medium containing the herbicide at a concentration ranging from 100–1000 nM.

2. The process according to claim 1, wherein the cytokinin is 6-benzylaminopurine.

3. The process according to claim 1, wherein the cytokinin is tidiazuron.

4. The process according to claim 1, wherein the frequency of recovered herbicide-tolerant transformed shoots as a percentage of the number of embryonic axes bombarded is about 10%.

5. The process according to claim 1, wherein the leguminous plant is selected from the group consisting of soybean, bean, cowpea and peanut.

6. The process according to claim 1, wherein the herbicide is an imidazolinone, the selecting is at a concentration of from about 500 to 100 nM, and the leguminous plant is soybean.

7. The process according to claim 1, wherein the herbicide is a glyphosate, the selecting is at a concentration of from about 300 to 1000 nM, and the leguminous plant is soybean.

8. The process according to claim 1, wherein the herbicide is an imidazolinone present at a concentration of from about 100 to 500 nM, and the leguminous plant is bean, cowpea or peanut.

9. The process according to claim 1, wherein the herbicide is a glyphosate and is present at a centration of from about 200 to 1000 nM, and the leguminous plant is bean, cowpea or peanut.

* * * * *

UNITED STATES PATENT AND TRADEMARK OFFICE
CERTIFICATE OF CORRECTION

PATENT NO. : 6,753,458 B1
DATED : June 22, 2004
INVENTOR(S) : Rech Filho et al.

It is certified that error appears in the above-identified patent and that said Letters Patent is hereby corrected as shown below:

<u>Title page,</u>
Item [73], Assignee, change "EMBRAPA-Empress" to read
-- EMBRAPA-Empresa --

Signed and Sealed this

Fourteenth Day of December, 2004

JON W. DUDAS
*Director of the United States Patent and Trademark Office*